(12) United States Patent
Ward et al.

(10) Patent No.: US 8,241,311 B2
(45) Date of Patent: Aug. 14, 2012

(54) METHODS AND SYSTEMS FOR BYPASSING AN OCCLUSION IN A BLOOD VESSEL

(75) Inventors: Sean Ward, Dublin (IE); Fiachra Sweeney, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 179 days.

(21) Appl. No.: 12/637,859

(22) Filed: Dec. 15, 2009

(65) Prior Publication Data
US 2011/0144677 A1    Jun. 16, 2011

(51) Int. Cl.
*A61B 17/32* (2006.01)
*A61F 2/06* (2006.01)

(52) U.S. Cl. ........ 606/159; 606/108; 606/170; 606/185; 606/194; 623/1.11; 128/898

(58) Field of Classification Search .............. 606/108, 606/159, 185, 191, 194; 604/164.01, 164.04, 604/164.06, 164.09, 164.1, 164.13
See application file for complete search history.

(56) References Cited

U.S. PATENT DOCUMENTS

| | | | |
|---|---|---|---|
| 5,458,639 A | 10/1995 | Tsukashima et al. | |
| 6,500,147 B2 | 12/2002 | Omaleki et al. | |
| 6,511,458 B2 | 1/2003 | Milo et al. | |
| 6,551,314 B1 | 4/2003 | Hill et al. | |
| 6,554,795 B2 | 4/2003 | Bagaoisan et al. | |
| 6,682,542 B2 | 1/2004 | Harkrider | |
| 6,736,827 B1 | 5/2004 | McAndrew et al. | |
| 7,169,160 B1 | 1/2007 | Middleman et al. | |
| 7,179,270 B2 * | 2/2007 | Makower | 606/159 |
| 2004/0167554 A1 * | 8/2004 | Simpson et al. | 606/159 |
| 2007/0265596 A1 * | 11/2007 | Jen et al. | 604/528 |
| 2008/0154172 A1 | 6/2008 | Mauch | |
| 2008/0243065 A1 | 10/2008 | Rottenberg et al. | |

* cited by examiner

*Primary Examiner* — Elizabeth Houston
*Assistant Examiner* — Sarah Webb

(57) ABSTRACT

Methods and systems for re-entering the true lumen of a vessel after subintimally bypassing an occlusion in a blood vessel. A guidewire is positionable within a subintimal tract in a wall of the blood vessel with a distal end located beyond the occlusion. A hollow lumen of the guidewire includes a retractable blade slidably exposable adjacent a distal end thereof for rotary cutting or scoring the intima layer of the vessel wall to create a transverse cut or line of weakness in the intima. A balloon catheter is subsequently trackable over the guidewire and once inflated tears or otherwise ruptures the transverse cut, thereby creating or enlarging a passageway into the true lumen of the blood vessel beyond the occlusion.

13 Claims, 6 Drawing Sheets

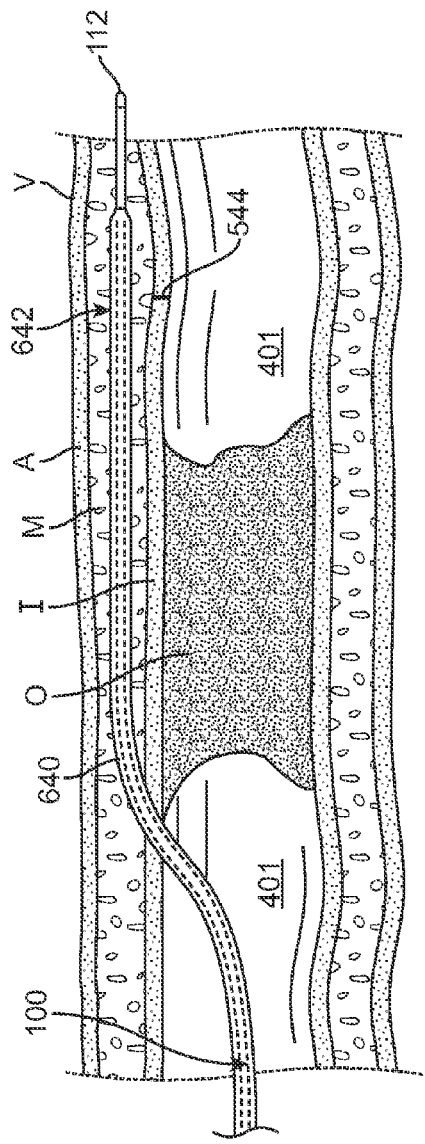
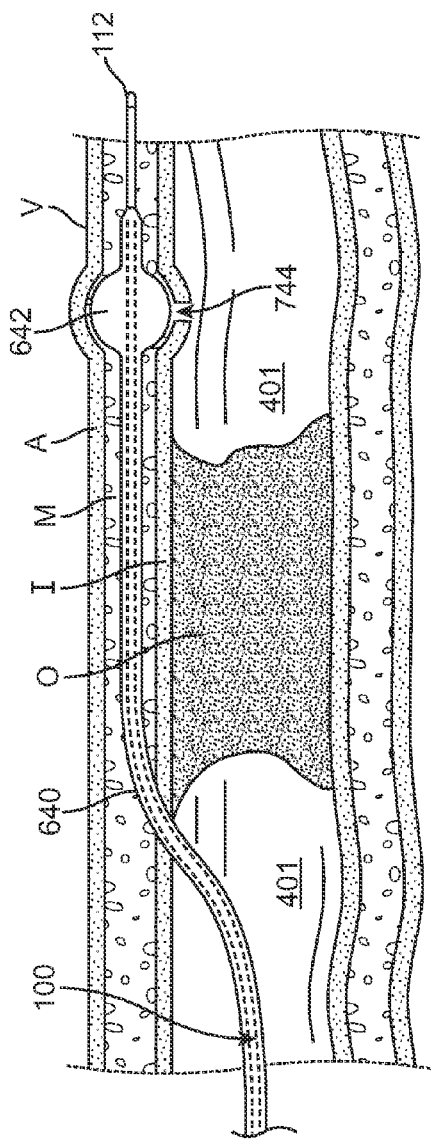
FIG. 6
FIG. 7

METHODS AND SYSTEMS FOR BYPASSING AN OCCLUSION IN A BLOOD VESSEL

FIELD OF THE INVENTION

The invention relates generally to a low profile guidewire system and a method of using the system for subintimally bypassing a blockage in a blood vessel such as a chronic total occlusion and reentering the true lumen of the blood vessel beyond the blockage.

BACKGROUND OF THE INVENTION

Cardiovascular disease, including atherosclerosis, is the leading cause of death in the United States. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often a patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the interventionalist can successfully recannalize a CTO is the interventionalist's ability to advance a suitable guidewire from a position within the true lumen of the artery proximal to the CTO lesion, across the CTO lesion, i.e., either through the lesion or around it, and then back into the true lumen of the artery at a location distal to the CTO lesion.

In some cases, such as where the artery is totally occluded by hard, calcified atherosclerotic plaque, the guidewire may tend to deviate to one side and penetrate through the intima of the artery, thereby creating a neo-lumen called a "subintimal tract" i.e., a penetration tract formed within the wall of the artery between the intima and adventitia. In these cases, the distal end of the guidewire may be advanced to a position distal to the lesion but remains trapped within the subintimal tract. In such instances, it is then necessary to divert or steer the guidewire from the subintimal tract back into the true lumen of the artery at a location distal to the CTO lesion. The process of manipulating the guidewire to reenter the artery lumen is often difficult and solutions have been proposed utilizing various means for dealing with such a problem.

A number of catheter-based devices have been heretofore useable to redirect subintimally trapped guidewires back into the true lumen of the artery. Included among these are a variety of catheters having laterally deployable cannulae, i.e., hollow needles. These catheters are advanced into the subintimal tract over the subintimally trapped guidewire, and the laterally deployable cannula is advanced from the catheter into the true lumen of the blood vessel, downstream of the CTO. A second guidewire is then passed through the laterally deployed cannula and is advanced into the true lumen of the artery. The laterally deployed cannula is then retracted into the catheter and the catheter is removed, along with the original guidewire, leaving just the second guidewire in place. This second guidewire is then useable to facilitate enlargement i.e., balloon dilation, atherectomy, etc., and/or stenting of the subintimal tract, thereby creating a subintimal reentry conduit around the CTO. Commercially available catheters of this type have been used successfully in the treatment of CTOs in relatively large vessels, such as the femoral artery, popliteal artery, etc. For example, the PIONEER® catheter system by Medtronic, Inc. utilizes a penetrator that exits through a side exit port of the catheter to puncture the intimal layer distal of the CTO to re-enter the true lumen of the vessel. However, their use in smaller diameter vessels, i.e., coronary arteries or below-the-knee applications, has been limited to date due to their relatively large diameter. Accordingly, there exists a need in the art for a low profile device and method of using such for treatment of a CTO in smaller diameter vessels, such as those located below the knee of a patient.

BRIEF SUMMARY OF THE INVENTION

Embodiments hereof are directed to a method for reentering a blood vessel downstream or distal of an occlusion. The blood vessel has a wall and an extraluminal or subintimal tract that has been formed in the wall, either naturally or manually, adjacent to the occlusion. The distal end of a subintimal reentry guidewire is transluminally advanced through the subintimal tract from a near side of the occlusion to a position in the subintimal tract on a far side of the occlusion. A cutting blade is then exposed through a distal side port of the subintimal reentry guidewire. With the cutting blade exposed, the subintimal reentry guidewire is rotated to create a transverse cut through an intimal layer of the vessel wall. The cutting blade is then retracted back into the subintimal reentry guidewire and a balloon is advanced over the subintimal reentry guidewire to a point adjacent the transverse cut in the intimal layer of the wall. The balloon is inflated to enlarge the transverse cut in the intimal layer of the wall and thereby create a subintimal reentry passageway through the intimal layer.

In another embodiment hereof, a subintimal reentry guidewire includes an elongated hollow guidewire shaft and an elongated core element slidingly disposed through a lumen of the hollow guidewire shaft. A retractable cutting blade positioned at a distal end of the core element is operable to deploy to an exposed position in which the cutting blade extends beyond an outer surface of the guidewire shaft through a distal side port of the guidewire shaft. The subintimal reentry guidewire is rotatable to circumferentially cut the vessel wall when the cutting blade is in the exposed position.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 4-10 illustrate the steps of utilizing the subintimal reentry guidewire of FIG. 1 to bypass a chronic total occlusion according to an embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as smaller diameter peripheral or coronary arteries, the invention may also be used in any other body passageways where it is deemed useful. Although the description of the invention generally refers to a system and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow if access is available from that direction. In other terms, the system and method described herein may be considered to bypass a vessel blockage from a near side of the blockage to a far side of the blockage. Furthermore, there is no intention to be bound by any expressed or implied theory presented in the preceding technical field, background, brief summary or the following detailed description.

Figure 1:
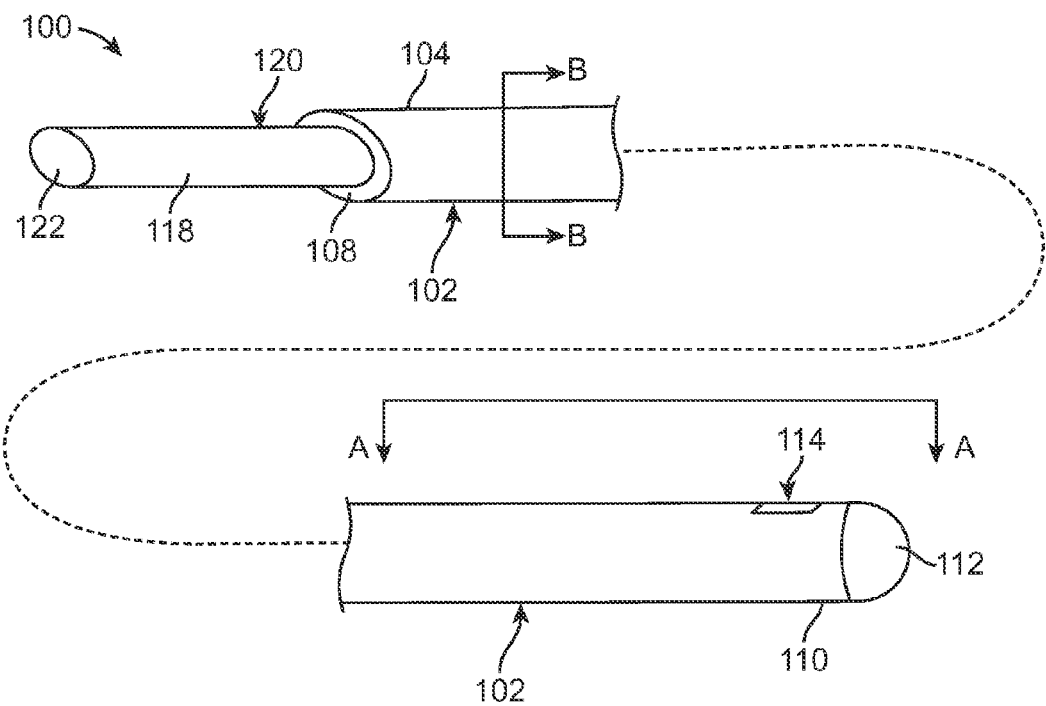
FIG. 1 is a schematic perspective view of a subintimal reentry guidewire according to an embodiment hereof, wherein a blade of the subintimal reentry guidewire is in a retracted or delivery configuration.
Figure 1A:
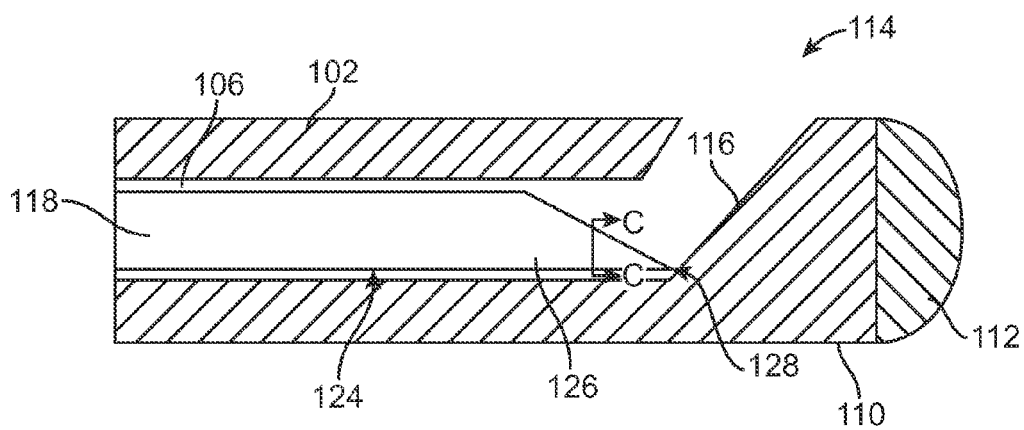
FIG. 1A is a sectional view taken along line A-A of FIG. 1.
Figure 1B:
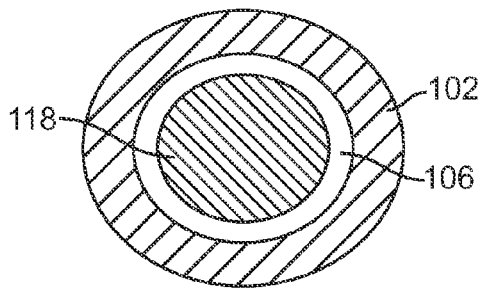
FIG. 1B is a cross-sectional view taken along line B-B of FIG. 1.
Figure 2:
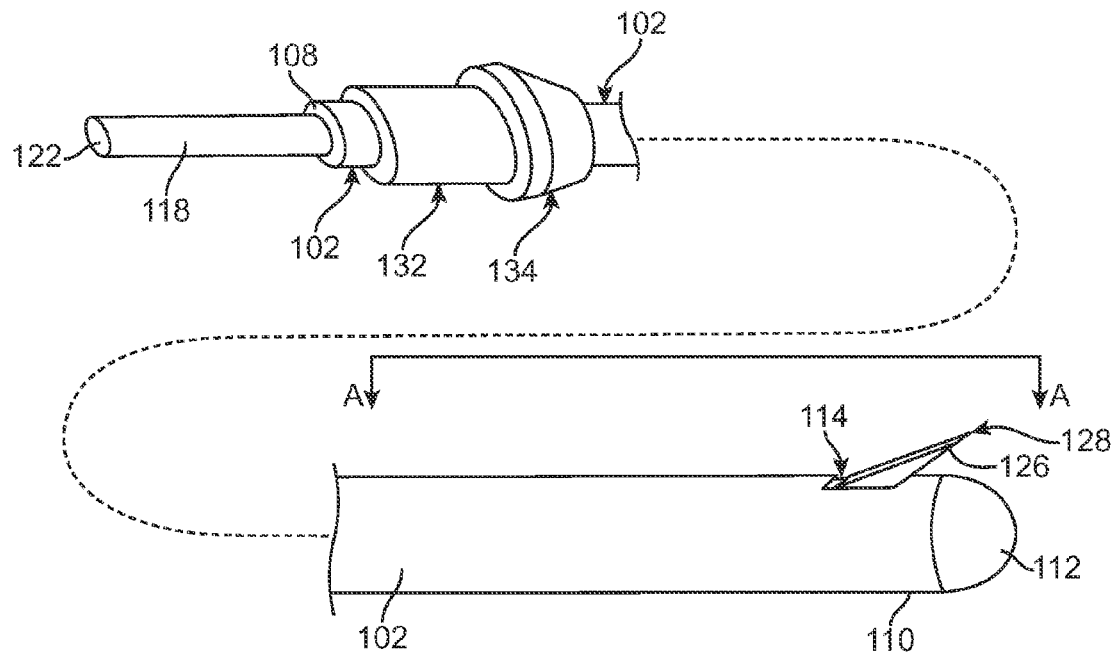
FIG. 2 is a schematic perspective view of the subintimal reentry guidewire of FIG. 1, wherein a blade of the subintimal reentry guidewire is in an exposed or deployed configuration.
Figure 2A:
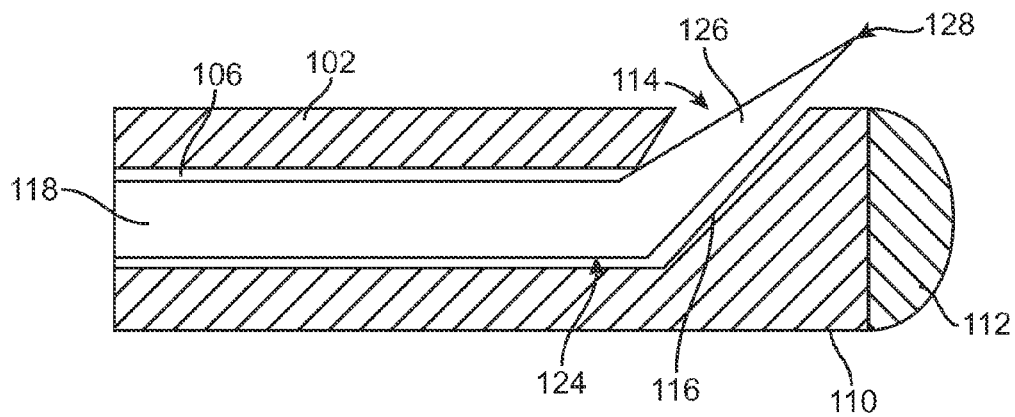
FIG. 2A is a sectional view taken along line A-A of FIG. 2.
Figure 2B:
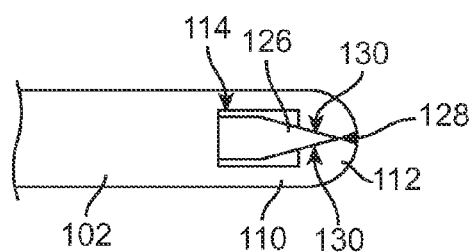
FIG. 2B is a top view of a distal portion of the subintimal reentry guidewire as shown in FIG. 2.

Embodiments hereof relate to a system and method for re-entering the true lumen of a vessel after subintimally bypassing an occlusion in a blood vessel such as a chronic total occlusion (CTO) of an artery. A true lumen reentry tool or subintimal reentry guidewire 100 utilizes a retractable blade to create a transverse cut in the intima of the blood vessel that splits open in response to inflation of a balloon of a conventional balloon catheter. The low profile of subintimal reentry guidewire 100 allows access to and treatment of occlusions occurring in very small diameter vessels that may not normally be accessed by reentry catheters with larger profiles. FIGS. 1, 1A, and 1B illustrate subintimal reentry guidewire 100 with the blade in a retracted position, and FIGS. 2, 2A & 2B illustrate subintimal reentry guidewire 100 with the blade in an exposed or working position.

Referring to FIGS. 1, 1A, and 1B, subintimal reentry guidewire 100 includes a hollow guidewire shaft 102 having an elongate tubular body 104 extending from a proximal end 108 that extends proximally outside of the patient's body to a distal end 110 that is positionable at the point of treatment, i.e., the site of a chronic total occlusion. Guidewire shaft 102 defines a lumen 106 that extends from proximal end 108 of guidewire shaft 102 and terminates at a distal side opening or port 114 formed through the sidewall of elongate tubular body 104. Distal side port 114 is located proximally adjacent to distal end 110 of guidewire shaft 102. Guidewire shaft 102 has a small outer diameter equal to or less than 0.014 inch such that subintimal reentry guidewire 100 has a low profile. In another embodiment, guidewire shaft 102 may have an outer diameter in the range of 0.014 inch to 0.035 inch. In various embodiments, guidewire shaft 102 has a wall thickness in the range of 0.001 inch-0.010 inch with lumen 106 having a diameter ranging from 0.005 inch to 0.025 inch. A rounded, atraumatic tip 112 may be attached to distal end 110 of guidewire shaft 102 to prevent damage to the vessel and facilitate advancement of guidewire shaft 102 through the through the vasculature. In other embodiments, guidewire tip 112 may have other configurations, such as a tapered core wire surrounded by a coil spring, as disclosed in U.S. Pat. No. 4,454,390 to Leary, which is incorporated herein in its entirety. Tip 112 may have an elongated taper which may be bent into any shape desired by a clinician. In one embodiment, tip 112 is a separate component that is attached to guidewire shaft 102 and may be formed from a soft flexible polymeric material such as polyethylene terephthalate (PET), polypropylene, nylon, polyethylene, polyether block amide (PEBA), fluoropolymers such as polytetrafluoroethylene (PTFE) or fluorinated ethylene propylene (FEP), or combinations thereof. Tip 112 and guidewire shaft 102 may be coupled together by any suitable means known to those skilled in the art, for example and not by way of limitation, welding, adhesive, or mechanical coupling. In another embodiment (not shown), tip 112 may be integrally formed with guidewire shaft 102 as a unitary structure.

A core element 118 is slidably disposed through lumen 106 of guidewire shaft 102. Core element 118 has an elongated cylindrical body 120 extending between a proximal end 122 and a distal end 124. Core element 118 is a solid wire-like element having a circular cross-section as shown in FIG. 1B. In another embodiment, core element 118 may have a hollow tubular body. When utilized in conjunction, hollow guidewire shaft 102 with core element 118 located therein have sufficient column strength to be pushed through a patient's vascular system without kinking and are also flexible enough to avoid damaging the blood vessel or other body lumen through which they are advanced. Hollow guidewire shaft 102 and core element 118 may be constructed from stainless steel, Co—Ni—Cr—Mo super alloy, NiTi alloys such as nitinol, and other suitable materials.

Figure 1C:
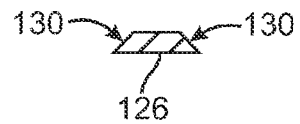
FIG. 1C is a cross-sectional view taken along line C-C of FIG. 1A.

A retractable cutter or cutting blade 126 is positioned at distal end 124 of core element 118. Cutting blade 126 is a relatively flat or planar element having at least one sharp cutting edge 130 operable to cleanly cut or slice through the intima of a vessel wall. Cutting blade 126 terminates in a pointed end or tip 128. As best shown in FIG. 1C, which is a cross-sectional view of cutting blade 126 taken along line C-C in FIG. 1A, cutting edges 130 are beveled edges forming an approximately 45 degree slope between the side surfaces or faces of blade 126. In other embodiments, cutting edges 130 of blade 126 may not include a bevel and/or may include only one cutting edge 130. In an embodiment, cutting edges 130 longitudinally taper to tip 128 resulting in a generally triangular cutting blade 126, as shown in a top view of cutting blade 126 in FIG. 2B. In an embodiment, the portion of cutting blade 126 that extends outside of the guidewire shaft 102 is approximately 0.1 mm-0.2 mm in length. In the embodiment of FIGS. 1 and 2, cutting blade 126 is integrally formed with core element 118. As such, the distal end of core element 118 may be stamped in a die or ground down to form cutting blade 126. In another embodiment (not shown), cutting blade 126 is a separate component that is attached to core element 118 and may be formed from a material such as stainless steel or an elastic or pseudo-elastic material such as a nickel-titanium alloy (nitinol). In such embodiments, cutting blade 126 and core element 118 may be coupled together by other means known to those skilled in the art, for example and not by way of limitation, soldering, welding, adhesive, or mechanical coupling. As shown in FIGS. 1 and 1A, cutting blade 126 may be maintained within lumen 106 of guidewire shaft 102 during delivery while guidewire shaft 102 is advanced through the vasculature.

Cutting blade 126 is operable to alternate between a retracted position in which cutting edges 130 of cutting blade 126 are within lumen 106 of guidewire shaft 102 as shown in FIGS. 1 and 1A, and an exposed position in which cutting edges 130 of cutting blade 126 extend transversely from distal side port 114 of guidewire shaft 102 as shown in FIGS. 2 and 2A such that cutting blade 126 extends beyond an outer surface of guidewire shaft 102. To deploy or expose cutting blade 126, core element 118 is distally advanced within guidewire shaft 102 causing cutting blade 126 to push against an inclined surface or ramp 116 formed adjacent distal side port 114. Ramp 116 deflects cutting blade 126 through side port 114 to the exposed or working position outside of guidewire shaft 102. In addition, since ramp 116 is at an incline, it causes cutting blade 126 to be positioned outside of guidewire shaft 102 with cutting edges 130 at a 30° to 45° angle as shown in FIG. 2. In another embodiment, ramp 116 may have an arc or curved shape such that cutting blade 126 exits side port 114 of guidewire shaft 102 at closer to a 90° angle.

In an embodiment, cutting blade 126 may be formed of a biocompatible resilient metal such as spring temper stainless steel or nitinol, which utilizes the pseudo-elastic properties of stress induced martensite. During deployment, cutting blade 126 is expected to be bent, without plastic deformation, to the angled configuration of FIG. 2 as cutting blade 126 is pushed over ramp 116. Once cutting blade 126 is retracted into shaft lumen 106 through distal port 114, cutting blade 126 resumes its straight, delivery configuration by its own internal restoring forces. Alternatively, cutting blade 126 may be pre-formed in a bent or curved shape that is elastically restrained in a straight, delivery configuration within guidewire shaft 102. A heat or thermal treatment of the selected alloy may be used to set the shape of cutting blade 126. When cutting blade 126 is deployed through port 114, it is expected to resume its pre-formed cutting configuration by its own internal restoring forces without a necessity of a ramp 116. Examples of medical devices incorporating pre-formed core elements employing the super elastic properties of stress induced martensite and being slidably disposed within an outer shaft having a side port may be found in U.S. Pat. No. 7,169,160 to Middleman et al., which is incorporated herein by reference. An actuator (not shown) located at proximal end 122 of core element 118 may be utilized to control deployment of cutting blade 126. For example, a knob or push-pull handle attached at proximal end 122 of core element 118 may be moved in the distal direction to cause advancement of core element 118 relative to guidewire shaft 102 to deploy cutting blade 126 and may be moved in the proximal direction to cause retraction of core element 118 relative to guidewire shaft 102 to retract cutting blade 126. Graduation markings (not shown) on the proximal end of core element 118 may be included to indicate to the user the distance that cutting blade 126 extends out of distal port 114.

When cutting blade 126 is in a working position as shown in FIGS. 2 and 2A, a removable locking device or wire torquer 132 is slidingly placed over proximal end 108 of guidewire shaft 102 to lock the longitudinal position of core wire 118 relative to guidewire shaft 102. To this end wire torquer 132 may be tightened or screwed via a knob 134 located thereon to compress guidewire shaft 102 onto core element 118, thereby clamping guidewire shaft 102 and core element 118 together to lock core element 118 and the exposed cutting blade 126 in the working position. As such, once cutting edges 130 of cutting blade 126 have been exposed as desired, clamping wire torquer 132 to guidewire shaft 102 prevents further inadvertent advancement of core element 118 relative to guidewire shaft 102 and thus prevents further inadvertent extension of cutting blade 126 out of distal port 114. In addition, locking guidewire shaft 102 and core element 118 together with wire torquer 132, or other such device, allows subintimal reentry guidewire 100, i.e., guidewire shaft 102 and the exposed cutting blade 126, to be rotated as an ensemble structure in order to circumferentially score or cut into the intima of a vessel wall as will be explained in more detail below.

Optionally, subintimal reentry guidewire 100 may incorporate one or more radiopaque markers that are strategically located on elongate body 104 of guidewire shaft 102 to be imageable by an imaging apparatus for aiding a clinician in delivery of subintimal reentry guidewire 100 to a correct rotational position or orientation for properly advancing cutting blade 126 from guidewire shaft 102 at the treatment site.

Figure 3:
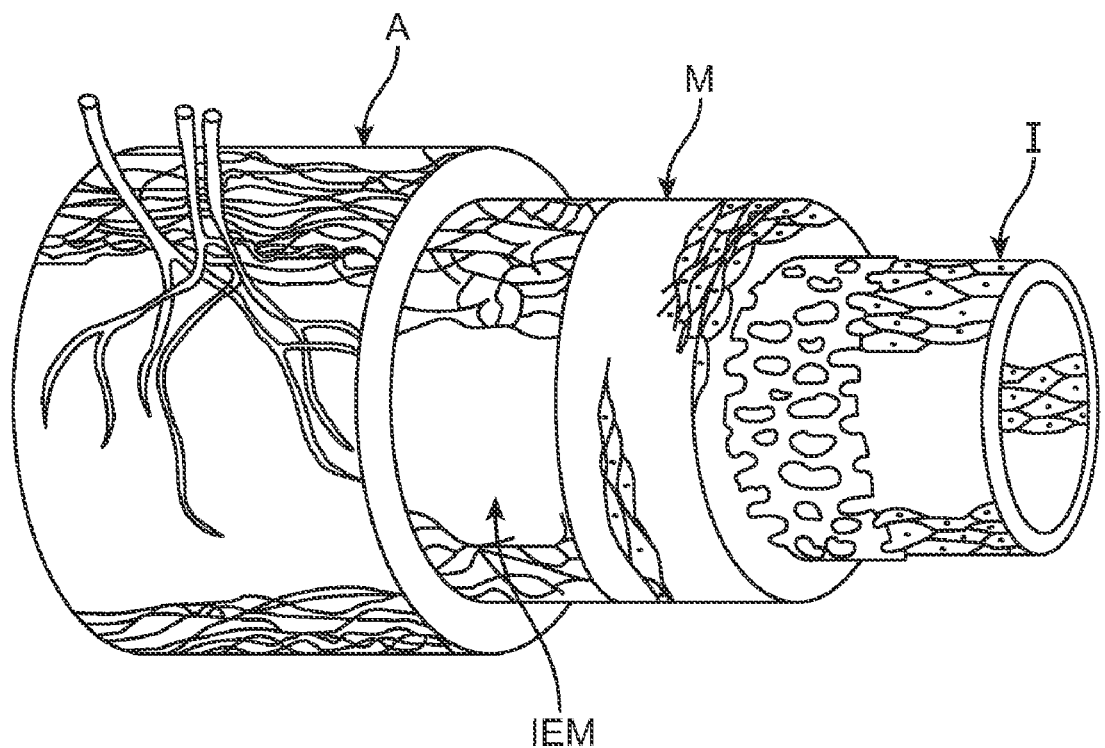
FIG. 3 is a diagram of an artery showing the three layers of tissue that comprise the artery wall.

FIG. 3 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood.

FIGS. 4-10 illustrate a prophetic method of using the above-described subintimal reentry guidewire 100 to bypass a chronic total occlusion O according to an embodiment hereof. Subintimal reentry guidewire 100 is used as part of a system for creating a subintimal reentry conduit within a wall of a blood vessel V, such as an artery located below the knee of a patient, to allow blood flow around the occlusion. Although described in relation to bypassing a chronic total occlusion O, it should be understood that the methods and apparatus described herein may be used for bypassing any tight stenoses in arteries or other anatomical conduits and are not limited to total occlusions. Typically, a guiding catheter and/or an introducer sheath (not shown) are first inserted percutaneously into a femoral artery of a patient. Subintimal reentry guidewire 100 is inserted into the guiding catheter and maneuvered through the vasculature to a treatment site, which in this instance is shown as a total occlusion O within a lumen 401 of blood vessel V. During delivery while subintimal reentry guidewire 100 is advanced through the vasculature, cutting blade 126 is maintained within lumen 106 of guidewire shaft 102.

Figure 4:
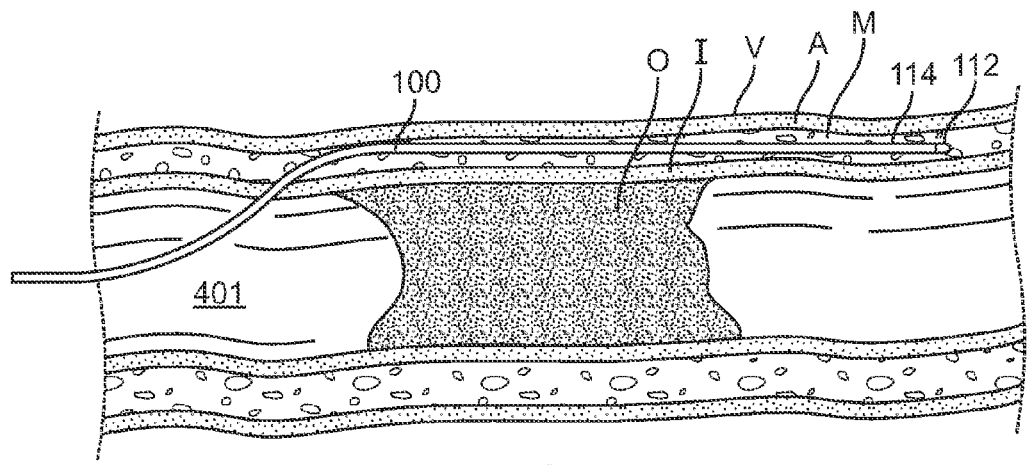

Referring to FIG. 4, in accordance with techniques known in the field of interventional cardiology and/or interventional radiology, subintimal reentry guidewire 100 is transluminally advanced through lumen 401 of blood vessel V to a position upstream of occlusion O. Subintimal reentry guidewire 100 pierces the intima I and is advanced distally to create a subintimal tract T by locally dissecting or delaminating intima I from media M or by burrowing through media M. In order to pierce the intima I, a clinician may manipulate the distal end of subintimal reentry guidewire 100 by prolapsing or bending-over the distal end of subintimal reentry guidewire 100 and thereafter may use the stiffer arc of the prolasped distal end to pierce into the intima I to advance subintimal reentry guidewire 100 there through. The piercing of the intima I is aided by the fact that typically blood vessel V is diseased, which in some instances makes the intima I prone to piercing. Subintimal reentry guidewire 100 is transluminally advanced within the subintimal tract T from a near side of occlusion O to a position where distal port 114 of subintimal reentry guidewire 100 is positioned in the subintimal tract on a far side of occlusion O. If one or more optional radiopaque markers are present, they may be used by the operator to make any necessary adjustment of the rotational orientation of subintimal reentry guidewire 100 within the subintimal tract T to ensure that cutting blade 126 will be deployed into a specific radial location, i.e. into the intima I, on the vessel wall.

Alternatively, another device other than subintimal reentry guidewire 100 may be initially used to create the subintimal tract T. Those of ordinary skill in the art will appreciate and understand the types of alternative devices that may be used in this step including an apparatus known as an "olive", a laser wire, an elongate radiofrequency electrode, or any other device suitable for boring or advancing through the vessel tissue. If an alternative device is used instead of subintimal reentry guidewire 100 to form the subintimal tract T, such alternative device may be removed and replaced with subintimal reentry guidewire 100 after the subintimal tract T has been formed.

Figure 5:
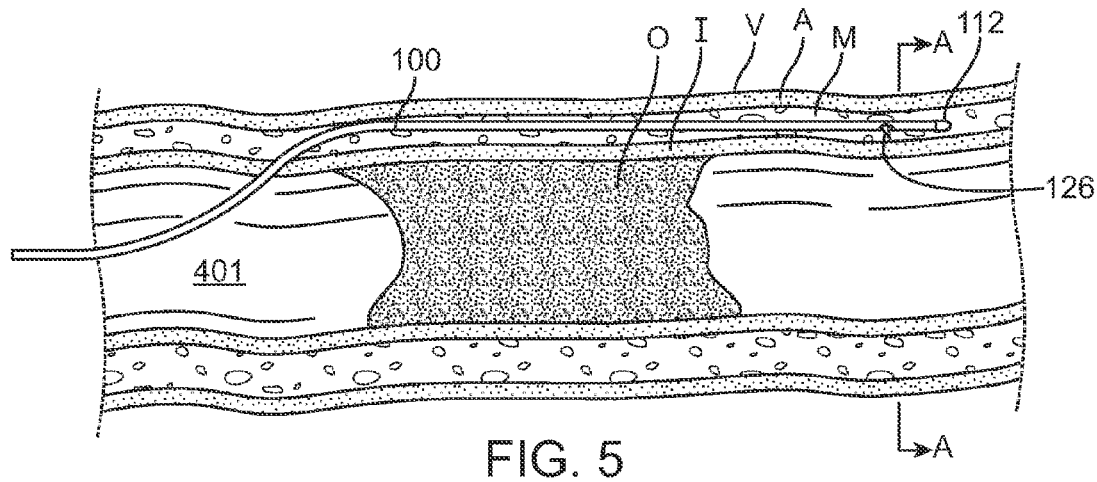
Figure 5A:
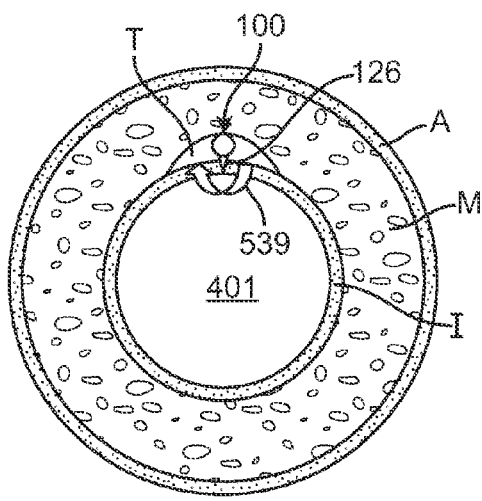
Figure 5B:
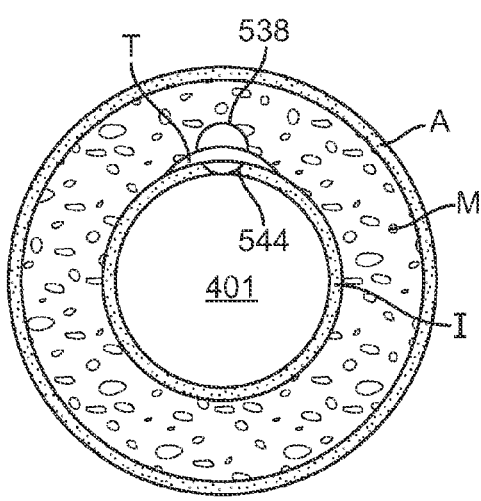

Once subintimal reentry guidewire 100 is positioned within the subintimal tract T with distal side port 114 downstream of occlusion O as desired, cutting blade 126 is exposed or deployed through distal side port 114 to extend beyond an outer surface of subintimal reentry guidewire 100 as shown in FIG. 5 and FIG. 5A, which is a schematic cross-sectional view taken along line A-A of FIG. 5. Cutting blade 126 is exposed by advancing core element 118 relative to guidewire shaft 102 and locking the longitudinal position of core element 118 with wire torquer 132 once cutting blade 126 is in its working position as described above. Subintimal reentry guidewire 100, i.e., guidewire shaft 102 and core element 118 with exposed cutting blade 126, is rotated in the direction of arrow 539 to create a circumferential cut 538 within the vessel wall on the far side of occlusion O, including a transverse cut 544 in the intima I. "Transverse" as used herein is intended to describe the portion of circumferential cut 538 made across the intima I at a right angle to the axis of blood vessel V, when subintimal reentry guidewire 100 makes a full or partial rotation around its longitudinal axis. FIG. 5B is a schematic cross-sectional view taken along the line A-A of FIG. 5, with subintimal reentry guidewire 100 removed for clarity, illustrating the resulting circumferential cut 538. Circumferential cut 538 is a slit or slice through the vessel tissue that does not result in the removal or tearing of the vessel tissue. As best shown in FIG. 5A, since cutting blade 126 is relatively short in length, it will cut through all or most of the thickness of the intima I but only slightly into the media M. As shown in FIGS. 5A and 5B, transverse cut 544 may have a depth that extends fully through the intima I into the true lumen 401 of the vessel. Such a full-depth transverse cut creates a narrow-width opening or slot through the intima I. In another embodiment (not shown), the transverse cut 544 has a depth that does not extend completely through the intima into the true lumen of the vessel. Such a partial-depth transverse cut creates a narrow-width groove or recess within the intima I. Further, in an embodiment hereof, subintimal reentry guidewire 100 is rotated approximately 360 degrees or one complete revolution to ensure that the intima I is cut. Such a complete revolution will result in circumferential cut 538 having a generally circular path as shown in FIG. 5B. In another embodiment hereof, subintimal reentry guidewire 100 may be rotated less than 360 degrees, e.g., between 120 and 180 degrees. Such a partial rotation may result in a cut that includes transverse cut 544 if the intima I is included in the arc of the rotation of subintimal reentry guidewire 100.

Cutting blade 126 is retracted proximally into lumen 106 via distal side port 114 of guidewire shaft 102 by retracting core element 118 as described above. A balloon catheter 640 having a balloon 642 mounted at a distal end thereof in a radially collapsed state is then advanced over subintimal reentry guidewire 100, through the subintimal tract T, to a position where balloon 642 is positioned on the far side of occlusion O and adjacent to or within transverse cut 544 in the intima I, as shown in FIG. 6. Balloon catheter 640 is a low-profile balloon dilation catheter sized to slidingly pass over subintimal reentry guidewire 100. Balloon catheters that may be adapted for use in embodiments hereof include those shown or described in U.S. Pat. Nos. 6,736,827; 6,554,795; 6,500,147; and 5,458,639, which are incorporated by reference herein in their entirety. Balloon catheter 640 may be an over-the-wire catheter or a rapid-exchange catheter. In an embodiment, a SPRINTER LEGEND RX dilatation catheter sold by Medtronic, Inc. of Minneapolis, Minn. may be adapted for used in methods hereof.

Referring to FIG. 7, balloon 642 of balloon catheter 640 is inflated within subintimal tract T adjacent transverse cut 544 to such an extent that it presses against intima I and causes transverse cut 544 to rupture or enlarge, thus creating a passageway 744 through intima I and a subintimal reentry conduit around occlusion O. Transverse cut 544 has a thickness of cutting blade 126 that when expanded by balloon 642 opens up into passageway 744, which may have a diameter of up to the diameter of balloon 642. Passageway 744 extends from the subintimal tract T into the true lumen 401 of vessel V. Transverse cut 544 in the intima I may thus be considered an area of weakness or a scored portion that splits or breaks open in response to inflation of a balloon of the conventional balloon catheter. Deployment of balloon 642 is accomplished by connecting a source of inflation fluid to an inflation port of balloon catheter 640 so that balloon 642 may be inflated as is known to one of ordinary skill in the art.

Figure 8:
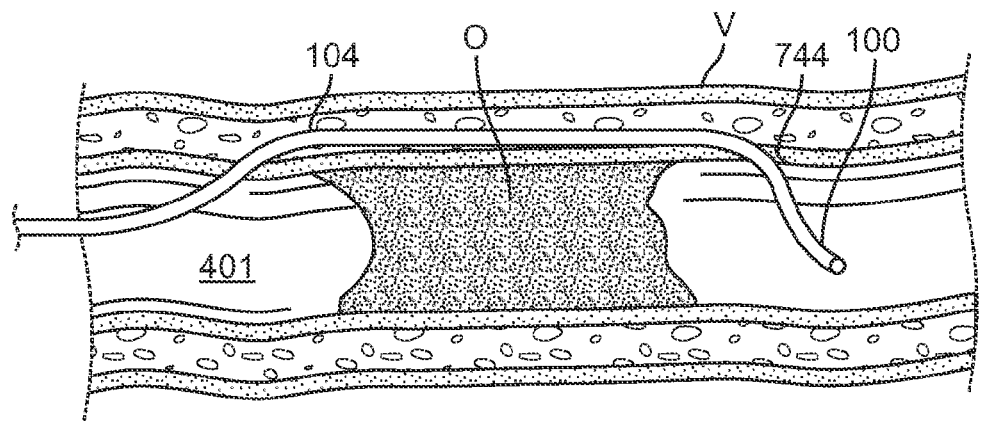

Thereafter, as seen in FIG. 8, balloon catheter 640 is proximally retracted and removed from the patient and subintimal reentry guidewire 100 having retracted cutting blade 126 therein is advanced through passageway 744, into true lumen 401 of vessel V distal to, i.e., downstream of, occlusion O. Subintimal reentry guidewire 100 extends in true lumen 401 proximal to occlusion O, through the subintimal tract T, and back into true lumen 401 distal to occlusion O such that occlusion O may now be successfully crossed via the subintimal conduit thus created. Due to the low profile of subintimal reentry guidewire 100, subintimal reentry conduits may be created around occlusions occurring in very small diameter vessels that may not normally be accessed by catheters with larger profiles.

Figure 9:
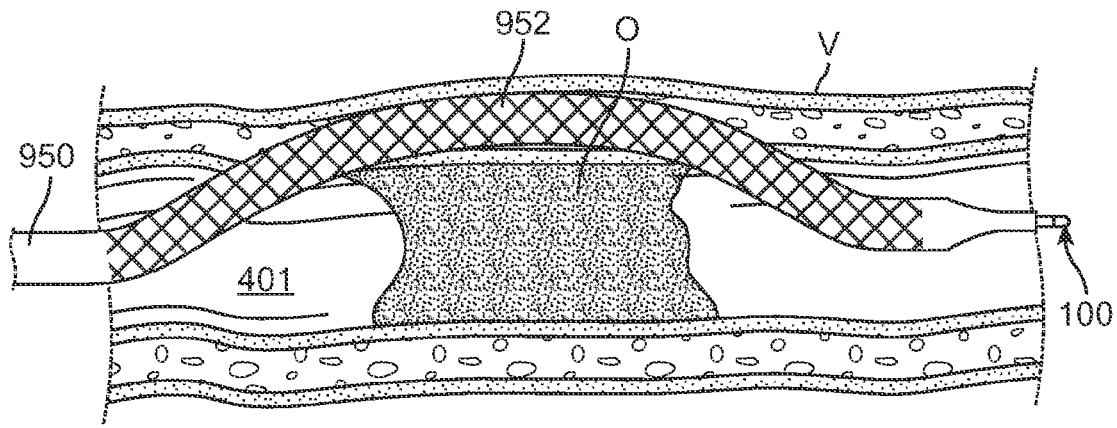
Figure 10:
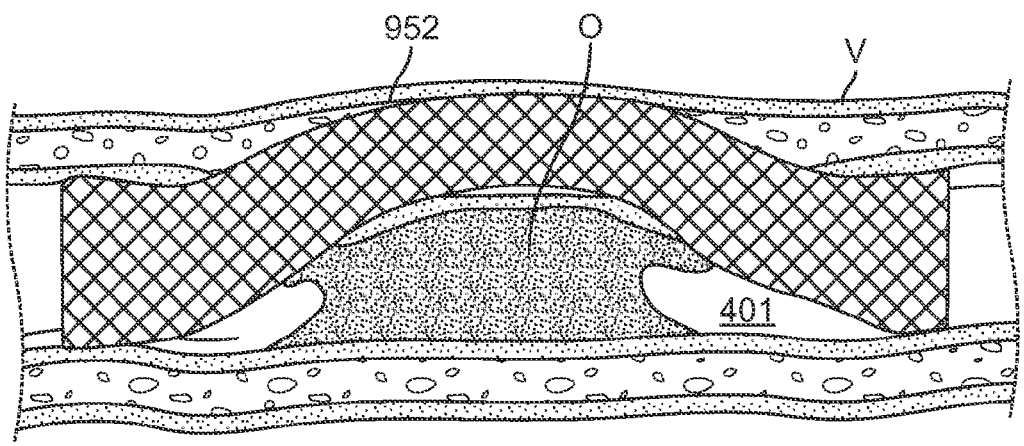

Optionally, a covered or uncovered stent may be placed within the subintimal reentry conduit to facilitate flow from the lumen of the vessel upstream of occlusion O, through the subintimal tract T and back into the lumen of the vessel downstream of occlusion O. For example, FIG. 9 shows a distal end of a catheter 950 having a stent 952 mounted thereon being advanced over subintimal reentry guidewire 100 to a position where a distal end of the radially collapsed stent 952 is in true lumen 401 of vessel V downstream of occlusion O, a proximal end of stent 952 is in true lumen 401 of vessel V upstream of occlusion O, and a mid-portion of stent 952 extends through the subintimal reentry conduit. Stent 952 is then deployed by either self-expansion or balloon inflation within the subintimal reentry conduit to dilate the subintimal reentry conduit and compress the adjacent occlusion O. Stent 952 provides a scaffold which maintains the subintimal reentry conduit in an open condition capable of carrying blood downstream of occlusion O. Thereafter, subintimal reentry guidewire 100 and catheter 950 may be removed from the patient, leaving stent 952 in an expanded configuration and creating a radially supported, subintimal blood flow channel around occlusion O as seen in FIG. 10. In some cases, it may be desirable to enlarge the diameter of the subintimal tract before advancing stent catheter 950 into and through it. Such enlargement of the subintimal tract may be accomplished by passing a balloon catheter over subintimal reentry guidewire 100 and inflating the balloon to dilate the tract, or may be any other suitable tract enlarging, dilating or de-bulking instrument that may be passed over subintimal reentry guidewire 100.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method for bypassing an occlusion in a blood vessel having a wall and a subintimal tract that has been formed in the wall adjacent to the occlusion, said method comprising the steps of:
    transluminally advancing a subintimal reentry guidewire through the subintimal tract from a near side of the occlusion to a position where a distal end of the subintimal reentry guidewire is positioned in the subintimal tract on a far side of the occlusion;
    extending a planar, generally triangular cutting blade transversely from a distal side port of the subintimal reentry guidewire to extend beyond an outer surface of the subintimal reentry guidewire;
    rotating the subintimal reentry guidewire with the cutting blade exposed to create a transverse cut in an intimal layer of the vessel wall on the far side of the occlusion;
    retracting the cutting blade proximally into the distal side port of the subintinial reentry guidewire;
    Advancing substantially an entire balloon over the subintimal reentry guidewire to the far side of the occlusion and adjacent the transverse cut in the intimal layer of the vessel wall; and
    inflating the balloon to enlarge the transverse cut in the intimal layer of the vessel wall thereby creating a passageway through the intimal layer.

2. The method of claim 1, wherein the transverse cut extends partially through the intimal layer of the wall.

3. The method of claim 1, wherein the transverse cut extends fully through the intimal layer of the wall.

4. The method of claim 1, wherein the step of rotating includes rotating the subintimal reentry guidewire approximately 360 degrees.

5. The method of claim 1, wherein the step of rotating includes rotating the subintimal reentry guidewire between 120 and 180 degrees.

6. The method of claim 1, further comprising the steps of:
    following the creation of the passageway through the intimal layer, advancing the subintimal reentry guidewire through the passageway to a position where the distal end of the subintimal reentry guidewire is positioned in a true lumen of the blood vessel on the far side of the occlusion;
    tracking a stent delivery catheter with a stent mounted thereon over the subintimal reentry guidewire until the stent extends from the true lumen on the near side of the occlusion through the subintimal tract and passageway and into the true lumen on the far side of the occlusion;
    deploying and radially expanding the stent; and,
    removing the stent delivery catheter and leaving the stent in place, such that fluid may flow from the true lumen of the blood vessel on one side of the occlusion through the stent and into the true lumen of the blood vessel on the other side of the occlusion.

7. The method of claim 1, wherein the blood vessel is an artery located in the leg of a human subject.

8. The method of claim 1, wherein the blood vessel is a coronary artery.

9. The method of claim 1, wherein the occlusion is a chronic total occlusion located in an artery.

10. The method of claim 1, wherein an outer diameter of the guidewire is no greater than 0.014 inches.

11. The method of claim 1, wherein the cutting blade is located at a distal end of a core element and the step of exposing the cutting blade includes distally advancing the core element within a lumen of the subintimal reentry guidewire and locking the core element into place relative to the subintimal reentry guidewire after the cutting blade extends out of the lumen of the subintimal reentry guidewire.

12. The method of claim 11, wherein distally advancing the core element includes pushing the cutting blade against an inclined surface formed within the subintimal reentry guidewire that guides the cutting blade to an angled configuration when the cutting blade is exposed.

13. The method of claim 11, wherein the cutting blade is formed of a biocompatible resilient material.

* * * * *